June 7, 1966 M. TRINTA Plant Pat. 2,642
WALNUT TREE
Filed March 1, 1965
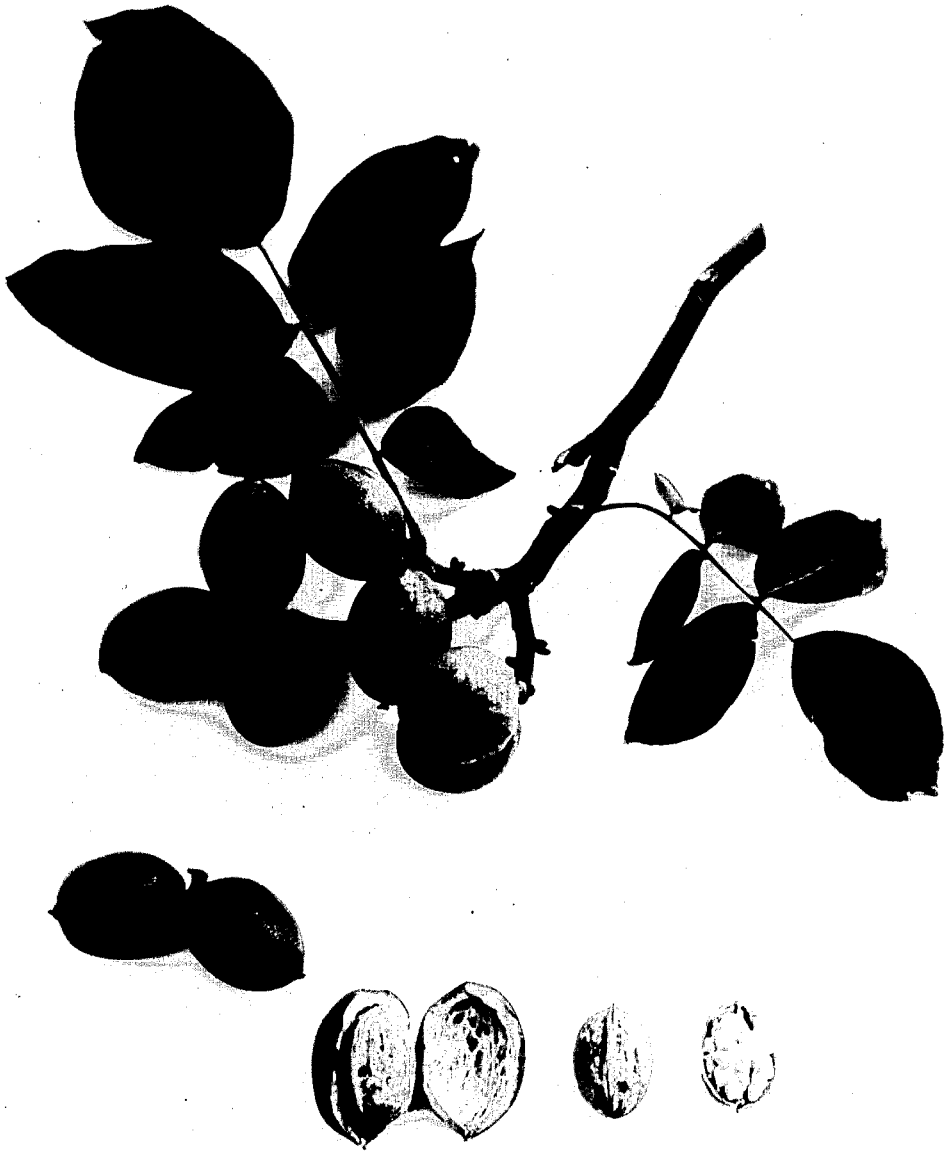
INVENTOR
Manuel S. Trinta
By Webster & Webster
ATTORNEYS United States Patent Office Plant Pat. 2,642
Patented June 7, 1966

2,642
WALNUT TREE

Manuel Trinta, Rte. 1, Box 58B, Patterson, Calif.

Filed Mar. 1, 1965, Ser. No. 436,385
1 Claim. (Cl. Plt.—32)

This discovery relates to a new and distinct variety of English walnut tree.

The present variety is characterized, as to novelty and in comparison to the Waterloo (unpatented)—which it most closely resembles—by earlier and heavier bearing, by larger and more abundant foliage, and by a blooming period as well as a harvesting period approximately two weeks earlier.

The variety is further characterized, as to novelty, by little susceptibility to blight or sunburn, which results in good nut quality; this, together with the aforementioned early and heavy bearing, making the variety extremely desirable for commercial planting.

I discovered the herein claimed variety of English walnut tree in an orchard located near Gustine, California, and which orchard included black walnut trees which had been grafted to what was believed to be all of the Waterloo variety but wherein one scion produced the instant variety.

Subsequent to my discovery of the variety and recognition by me of its novel characteristics, I asexually reproduced it in an orchard located near Patterson, California, by grafting on black walnut seedlings; such asexual reproductions, in maturity, having run true to the parent in all respects.

The drawing comprises an illustration, by photographic reproduction in color, of a twig with leaves and in-hull nuts; a pair of in-hull nuts, detached; a nut with the hull split open; a nut with the hull removed; and a kernel or meat remaining in a half shell.

Referring now more specifically to the botanical details of this new and distinct variety of English walnut tree, the following is an outline description thereof; all major color plate identifications, by comparison with fresh specimens, being by reference to Maerz and Paul Dictionary of Color, except where common terms of color definition are employed.

Tree:

*Parentage.*—Unknown.
*Size at maturity.*—Large, strong. Holds crop, slightly drooping.
*Growing habit.*—Moderately fast on a young tree, slows down as tree gets older.
*Adaptability.*—Well adapted to different soils.
*Vigor.*—Vigorous.
*Wood.*—Trunk: Smooth, gray. Branches: Smooth gray. Fruiting twigs: Short, light brown. Lenticels: Short, narrow, tan. Color of bark: Medium.
*Foliage.*—Density: Extremely heavy or dense. Time of leafing (date when tip buds average 1" in length) at Patterson, California, 1964—7 days after Payne; 17 days before Hartley; 22 days before standard Franquette.

The above three varieties are unpatented.

Leaves:

*Size.*—Vary large.
*Color of leaflets.*—Top side—medium green (23–L–8). Under side—lighter green (22–L–6). Rachis and prominent ribs on under side of leaves—greenish yellow (19–L–4).
*Margin of leaflets.*—Smooth, regular.
*Petiole.*—Very short.
*Glands.*—None.

Flowers:

*Age at which tree starts producing catkins.*—Very early.
*Number of catkins produced.*—Abundant.
*Size of catkins.*—Very large.
*Time of pollen shedding.*—Early.
*Age at which tree starts producing pistillate flowers.*—Very early.
*Number of pistillate flowers produced by young trees.*—Very abundant.
*Number of pistillate flowers produced by mature trees.*—Very abundant.
*Time when pistillate flowers are receptive.*—Midseason.
*Coincidence of staminate and pistillate bloom.*—Pollen shed late but considerable overlap of pistillate bloom.

Nuts:

*Yield.*—Very heavy.
*Quality.*—Moderately good.
*Maturity.*—Midseason.
*Evenness of maturity (period between time first and last nuts are ready to harvest).*—Short.
*Time of ripening.*—Medium.
*Date of first picking.*—Late September.
*Date of last picking.*—Early October.
*Tenacity.*—Nuts hang until shaken, then come with one shaking.
*Cluster.*—Substantial tendency to doubles, many triples.
*Size.*—Average–large.
*Weight of nuts.*—Average—31 in-shell nuts per pound.
*Uniformity of size.*—Little variation.
*Shape.*—Long cylindrical. Blossom end—beaked. Basal end—rounded.
*Color of shell.*—Medium. Slightly lighter than Eureka. Light tan (13–D–6).
*Thickness of shell.*—Thick.
*Seal.*—Very good.
*Roughness of shell.*—Medium.
*Husk or hull.*—Fairly thick. Medium green (22–L–7) flecked with lighter yellowish green (19–L–4).

Kernel:

*Flavor.*—Excellent.
*Shape.*—Oblong. Symmetric
*Texture.*—Smooth grain.
*Suture.*—Sharp.
*Size.*—Large. 48–50% meat.
*Fill.*—Very good.
*Plumpness.*—Plump.
*Color.*—Skin—light beige (11–I–3). Inside or cut—Ivory (9–B–1).
*Veining.*—Lightly veined.

Resistance to blight and sunburn: Moderate.

The tree and its nuts herein described may vary in slight detail due to climatic and soil conditions under which this variety may be grown; the present description being of the variety as grown in the Central Valley of California.

The following is claimed:

A new and distinct variety of English walnut tree, substantially as illustrated and described, characterized—in comparison to the Waterloo variety—by earlier and heavier bearing, by larger and more abundant foliage, and by a blooming period as well as a harvesting period approximately two weeks earlier.

No references cited.

ANTONIO F. GUIDA, *Acting Primary Examiner.*

ABRAHAM G. STONE, *Examiner.*

R. E. BAGWILL, *Assistant Examiner.*